United States Patent [19]

Nakamichi et al.

[11] Patent Number: 5,688,510
[45] Date of Patent: Nov. 18, 1997

[54] PROCESS FOR PRODUCING STABLE MEDICINAL COMPOSITION, AND PHARMACEUTICAL PREPARATION

[75] Inventors: Kouichi Nakamichi, Shiga; Shougo Izumi, Kyoto; Hiroyuki Yasuura, Shiga, all of Japan

[73] Assignee: Nippon Shinyaku CO. LTD., Japan

[21] Appl. No.: 648,174

[22] PCT Filed: Nov. 17, 1994

[86] PCT No.: PCT/JP94/01936

§ 371 Date: May 17, 1996

§ 102(e) Date: May 17, 1996

[87] PCT Pub. No.: WO95/13794

PCT Pub. Date: May 26, 1995

[30] Foreign Application Priority Data

Nov. 18, 1993 [JP] Japan ................... 5-289127

[51] Int. Cl.⁶ .................. A16K 35/78; A16K 9/20; A16K 9/00; A16K 9/14
[52] U.S. Cl. .................. 424/195.1; 424/6; 424/43; 424/46; 424/47; 424/490; 424/491; 424/492; 424/493; 424/494; 424/495; 424/496; 424/497; 424/498; 424/483; 424/484; 424/485; 424/486; 424/487; 424/488; 424/489

[58] Field of Search ................... 424/195.1, 6, 43, 424/46, 47, 483–489, 490–498; 514/951–53, 959, 960

[56] References Cited

U.S. PATENT DOCUMENTS

| | | | |
|---|---|---|---|
| 4,764,378 | 8/1988 | Keith et al. | 424/435 |
| 4,801,460 | 1/1989 | Goertz et al. | 424/465 |

FOREIGN PATENT DOCUMENTS

| | | | |
|---|---|---|---|
| 62-242630 | 10/1987 | Japan | A61K 47/00 |
| 62-265235 | 11/1987 | Japan | A61K 47/00 |

*Primary Examiner*—John W. Rollins
*Attorney, Agent, or Firm*—Graham & James LLP

[57] ABSTRACT

A process for producing a pharmaceutical composition is disclosed. In the process, 1 part by weight of a physiologically inert powdery additive, 0.001–1 part by weight of a macromolecular additive per part by weight of said insert powdery additive, and at least one drug substance are used as ingredients and processed en bloc by means of a multi-screw extruder. The drug substance used in the process can be selected from the following group: subliminable drug, volatile drug, drug hydrolyzable in the presence of water, drug which develops whiskers, and hygroscopic or deliquescent drug. The process confers increased physicochemical stability to the pharmaceutical composition and the drug substance contained therein.

14 Claims, 1 Drawing Sheet

FIG. 1

PROCESS FOR PRODUCING STABLE MEDICINAL COMPOSITION, AND PHARMACEUTICAL PREPARATION

TECHNICAL FIELD

The present invention relates to a process for producing physicochemically stable medicinal compositions.

BACKGROUND ART

Useful drugs are available for a variety of diseases but because of their inherent instability, certain drugs present the problem that they decompose during storage to cause discoloration of preparations or aggregation of granules by absorbing ambient moisture. Such objectionable events are frequently associated with heat, moisture, water, light, acids, bases, and/or air. It is generally thought that these factors are delicately involved in the unwelcome events mentioned above.

The conventional and common approach toward stabilizing any drug or preparation physically and chemically comprises identifying the instability factors involved and disposing of each of the factors. For sublimable drugs, a method comprising addition of a metal salt (German Patent 1034327, Japanese Patent Publication No.49-11219) or a method in which drugs are made amorphous (Japanese Patent Application Kokai S58-154547 and Japanese Patent Application Kokai S58-154548) is used. For drugs hydrolyzable in the presence of water, a method comprising addition of aluminum silicate and hydrolyzed starch and subsequent granulation-dehydration (Japanese Patent Kokai S60-89479) or a conventional coating method using a synthetic or natural film-forming polymer or a waxy substance. For drugs which would develop whiskers, a method comprising adding carbon, silicic anhydride and/or montmorillonite (Japanese Patent Publication No.56-37970), a method comprising adding an antacid (Japanese Patent Publication No. 2-85214), or a method in which granules containing a drug liable to develop whiskers and granules containing other substances are independently provided (Japanese Patent Publication No. 4-5234) is used. To overcome the inter-grain adhesion or dissolution of dosage forms associated with the hygroscopicity or deliquescence of drugs, a cyclodextrin clathrate method (Japanese Patent Application Kokai S 56-133236), a method employing an organic acid [Yakuzaigaku (Pharmaceutical Science) 47, No. 2, p. 87, 1987], and a method comprising using an excipient having a high water absorption capacity (the Proceedings of the 105 Congress of Pharmaceutical Society of Japan, p. 740), among others, are known.

However, it is often time-consuming to locate the individual instability factors involved and disposing of each of them. Moreover, many of the solutions so far proposed are not satisfactory in practical applicability, cost, production efficiency, operating conditions required, and quality. Thus, the conventional remedies are not fully satisfactory for commercial application.

Meanwhile, a multi-screw extruder or a screw kneader-extruder is in broad use in the food and plastics industries and mainly for the processing of food (cereals, proteins, animal meat, fish meat, etc.).

As technologies utilizing a multi-screw extruder in the pharmaceutical field, a process for producing solid pharmaceutical preparations (Japanese Patent Application Kokai S62-242630), a process for producing solid dispersions (PCT WO92/18106), a process for producing a wax matrix (PCT WO94/08568), and the process disclosed in Japanese Patent Application Kokai H5-194197 are known. These technologies are designed for expedient and commercially profitable manufacture of preparations useful for increased bioavailability and/or controlled release and not directly relevant to a technology for stabilizing drug substances.

DISCLOSURE OF INVENTION

A great commercial advantage should be realized if drugs and preparations could be stabilized in one operation against a plurality of factors affecting the stability of such drugs and preparations.

The present invention, therefore, has for its primary object to provide a technology by which drugs and preparations can be stabilized both physically and chemically in a practically feasible, economical, and expedient manner.

Exploring into many potentials of a multi-screw extruder (hereinafter referred to briefly as "extruder") in the pharmaceutical field, the inventors of the present invention happened to discover a means for producing pharmaceutical products satisfying the above-mentioned object and have ultimately developed the present invention.

The extruder essentially consists of a hollow cylindrical element known as barrel, a die constituting an exit, and a screw means. The barrel generally consists of a plurality of barrel zones and one or more screws extend through the barrel. The screws are available in various types such as the trapezoidal screw, trapezoidal cut screw, trapezoidal reverse cut screw, ball screw, kneading paddle (kneading disk), etc. and these types can be used in an optional combination. The load fed to the extruder is caused by the screws to advance within the barrel, in the course of which advance it is kneaded and otherwise processed, and is finally discharged from the orifice of the die. Usually, the temperature of each of the barrel zones and that of the die can be independently controlled. The extruder is a machine in which a plurality of screws cooperate or interfere with each other to physically generate a high energy output with which the load is processed.

In the practice of the present invention, any extruder having the fundamental functions of transportation, mixing, crushing, and heating of a water-rich or oil-rich load as used prevalently in the fields of food and plastics can be utilized as it is. Provided the extruder is equipped with two screws, the pharmaceutical composition of the present invention (hereinafter referred to as the composition of the invention) can be successfully manufactured.

The extruder is available in various types, such as the non-intermeshing, counter- or co-rotating extruder, the completely or partially intermeshing, counter- or co-rotating extruder, etc. In the practice of the present invention, the use of a completely intermeshing, co-rotating extruder is preferred and particularly the completely intermeshing, co-rotating extruder equipped with an axially disposed kneading paddle (kneading disk) is preferred.

The inventors of the present invention should be credited with the first who have ever succeeded in the physicochemical stabilization of drugs and preparations by means of an extruder.

The present invention is now described in detail,

The present invention relates to a pharmaceutical composition characterized by using 1 part by weight of a physiologically inert powdery additive, 0.001–1 part by weight of a macromolecular additive, and at least one drug selected from the following groups of drugs as essential ingredients and processing them en bloc with an extruder.

Groups of drugs (1) Sublimable drugs, (2) volatile drugs, (3) drugs hydrolyzable in the presence of water, (4) drugs liable to develop whiskers, and (5) hygroscopic or deliquescent drugs.

By processing a drug with an extruder judiciously to provide a pharmaceutical composition of the above formulation, both the drug and preparation can be physicochemically stabilized.

This extruder en bloc processing need not necessarily occur over the entire length of the barrel structure and the die. If the en bloc processing is achieved in a certain barrel zone and downstreams, the composition of the invention can be successfully provided.

The term "en bloc processing" is used throughout this specification to mean that the whole feed is subjected to the treatments offered by the extruder, such as shearing, mixing, kneading, compression, extrusion, etc.

The extruder en bloc processing of the whole feed can be achieved by several alternative methods, namely (1) the method in which all components of the feed are previously mixed and/or kneaded and fed to the extruder via its main feeding port, (2) "several components of the feed" are previously mixed and/or kneaded and fed to the extruder via its main feeding port and "the remainder of the feed" is fed via its auxiliary feeding port, and (3) the method in which "one component of the feed" is fed to the extruder via its main feeding port and "the remainder of the feed" is fed via an auxiliary feeding port. Depending on types of drugs, the first-mentioned method (1) is considered to be the most expedient method.

As used herein, the term "main feeding port" means the most fundamental inlet through which the processing load is fed into the barrel structure and the term "auxiliary feeding port" means a feeding inlet other than said main feeding port for supplemental feeding of, say, water and additives.

In method (1), other optional materials may be supplied through the auxiliary feeding port where needed.

In method (2), the drug and physiologically inert powdery additive, for instance, may constitute said "several components of the feed", while the macromolecular additive may constitute said "remainder of the feed". Or the physiologically inert powdery additive and the macromolecular additive, for instance, may constitute said "several components of the feed", while the drug, for instance, may constitute said "remainder of the feed". Among the preferred "several components of the feed" is the physiologically inert powdery additive. The "remainder of the feed" may be fed through the auxiliary feeding port either individually or as a mixture of any desired combination through a plurality of auxiliary feeding ports. It is also possible to include one or more of said "several components of the feed" in the "remainder of the feed" and further feed them through the auxiliary feeding port or ports.

In method (3), said "one component of the feed" may be any material excepting a liquid material but preferably is primarily the physiologically inert powdery additive. The "remainder of the feed" may be fed through one auxiliary feeding port or either individually or as a mixture through a plurality of feeding ports.

In the present invention, mixing and kneading can be carried out manually or mechanically using a kneader-mixer, a twin-shell blender, a double-cone mixer, a cubic mixer, a ribbon mixer or the like.

Supply of the feed into the barrel structure can be carried out either manually or by means of the feeder with which the extruder is usually provided and any device capable of supplying the feed at a constant rate can be utilized without particular limitation. The device as such includes a screw feeder, a table feeder, a slurry feeder, a pressure feeder, a belt-conveyorized constant-rate feeder, an electromagnetic feeder, and so on.

The proportion of said macromolecular additive is dependent on the other raw materials, mode of production, extruder type and model, etc. but is suitably in the range of 0.001 to 1 part by weight per part by weight of the physiologically inert powdery additive. The preferred range is 0.005–0.9 part by weight and the most preferred range is 0.01–0.6 part by weight. However, the composition of the invention can be produced, in some instances, even when the proportion is less than 0.001 part by weight or greater than 1 part by weight.

There is no particular limitation on the proportion of the drug in the feed but can suitably be in the range of 0.0001–10 times (by weight) the combined amount of said physiologically inert powdery additive and macromolecular additive. The preferred proportion is 0.001–5 times (by weight) and the most preferred range is 0.01–1 times (by weight). If it is less than 0.0001 times, no practically useful result may be obtained. If the proportion is more than 10 times, there will be cases in which the composition of the present invention cannot be manufactured.

The physiologically inert powdery additive is any substance that is commonly used in powdery form as an excipient in pharmaceutical practice and will not be degraded to any substantially extent in the course of extruder processing. Thus, for example, lactose, maltose, fructose, glucose, xylose, crystalline cellulose, low-substituted hydroxypropylcellulose, calcium hydrogenphosphate, mannitol, xylitol, sorbitol, granulated sugar, dried aluminum hydroxide gel, synthetic aluminum silicate, precipitated calcium carbonate, sodium hydrogen carbonate, talc, dextrin, cylodextrin, light anhydrous silicic acid, hydrous silicon dioxide, croscarmellose sodium, carmellose calcium, kaolin, carboxymethylstarch sodium, synthetic hydrotalcite, magnesium metasilicate aluminate, etc. can be mentioned. Furthermore, even starches which are liable to undergo aging depending on extruder parameter settings, such as corn starch, potato starch, wheat flour, rice flour, tapioka starch, etc. can also be used as said physiologically inert powdery additive only if parameter settings not causing such degradation are selected.

At least one species of said physiologically inert powdery additive can be employed. And even when two or more different species are employed, the composition of the invention can be successfully manufactured.

The macromolecular additive mentioned hereinbefore includes and is not limited to vinyl polymers, typically polyvinyl alcohol, polyvinylpyrrolidone, polyvinyl acetal diethylaminoacetate, carboxyvinyl polymers, etc.; acrylic polymers, typically poly(sodium acrylate), methacrylic acid copolymers, aminoalkyl methacrylate copolymers, etc.; cellulose derivatives such as methylcellulose, hydroxyethylcellulose, hydroxypropylcellulose, hydroxypropylmethylcellulose, carboxymethylcellulose sodium, etc.; naturally-occurring macromolecular substances such as gum tragacanth, gelatin, sodium alginate, pullulan, gum arabic powder, agar, gum xanthane, etc., chemically modified starches which are derived from various starches separated from plant sources such as corn, potato, rice, wheat, tapioka, arrowroot, etc., e.g. heat-treated starch, oxidized starch, acid-treated starch, enzyme-treated starch, glutinized starch, etc.; higher fatty acids which are solid at ordinary temperature but melt when heated, such as stearic acid, lauric acid, myristic acid, pentadecanoic acid, palmitic acid, margaric acid, nonadecanoic acid, arachic acid, behenic acid, lignoceric acid, cerotic acid, montanic acid, oleic acid, linoleic acid, linolenic acid, etc.; higher alcohols such as stearyl alcohol, cetanol, pentadecanol, hexadecanol, heptadecanol, eicosanol, cholesterol, etc.; polyhydric alcohols such as polyethylene glycol 4000, polyethylene glycol 6000, polyethylene glycol 20000, etc.; oleaginous materials such as carnauba wax, cacao butter, beef tallow, lard, paraffin, beeswax, microcrystalline wax, hydrogenated castor oil, etc.; and surfactants such as sucrose fatty acid esters, polyoxyethylene stearate, polyoxyethylene-polyoxypropylene glycol, glycerin monostearate, sorbitan monostearate, sorbitan monopalmitate, sodium lauryl sulfate, and lauromacrogol.

At least one species of the above-mentioned macromolecular additive can be employed, and the composition of the present invention can be successfully obtained by using two or more different species as well.

In the context of the present invention, the drug which can be physicochemically stabilized includes sublimable drugs, volatile drugs, drugs hydrolyzable in the presence of water, drugs which develop whiskers, and drugs which are hygroscopic or deliquescent.

The group of sublimable drugs includes but is not limited to sodium 1,4-dimethylisopropylazulene-3-sulfonate (hereinafter abbreviated as GASN), L-menthol, paraform, trimethadione, camphor, and naphthalene. The group of volatile drugs includes but is not limited to essential oils contained in aromatic crude drugs, such as cinnamyl alcohol, anethole, eugenol, etc., and flavors extracted from crude drugs, such as cinnamon oil, eucalyptus oil, lemon oil, fennel oil, clove oil, and mint oil. The group of drugs hydrolyzable in the presence of water includes but is not limited to aspirin, pipethanate hydrochloride, L-ethylcysteine hydrochloride, pyridostigmine bromide, calcium pantothenate, mepitiostane, pentobarbital sodium, and trichlorisocyanuric acid. The group of drugs which develop whiskers (whisker-shaped crystals that grow particularly when drugs are stored in sealed containers) includes but is not limited to ethenzamide, caffeine, acetaminophen, bromvalerylurea, and clofedanol hydrochloride. The group of hygroscopic or deliquescent drugs includes but is not limited to sodium valproate, cyanocobalamin, diethylcarbamazine citrate, isosorbide, diclofenac sodium, betahistine mesylate, carpronium chloride, tolazoline hydrochloride, reserpilic acid dimethylaminoethyl ester dihydrochloride, carbachol, choline theophyllinate, choline salicylate, citicoline, hexamethonium bromide, chlorophyllin sodium-copper salt, panthenol, dexamethazone phosphate disodium salt, plant extracts (Querci Folium extract, Mallot Cortex extract, Equisetum arvense extract, etc.), procainamide hydrochloride, L-proline, and calcium chloride.

At least one of the above-mentioned drugs can be employed.

The composition of the invention can be produced with addition or inclusion of a solvent depending on the type of drug. There are cases in which the use of a solvent leads to better results. By using a solvent, the kneading and shear actions within the barrel can be improved and enhanced so that the physiochemical stability of the drug and preparation can be enhanced. The processing efficiency may also be improved. It is preferable to use water or an organic solvent when, for example, the drug is not liable to be hydrolyzed or neither hygroscopic nor deliquescent. On the other hand, when the drug is liable to be hydrolyzed or hygroscopic or deliquescent, it is preferable to avoid using water and any organic solvent and, instead, to use a plasticizer and/or a fluidizing agent.

The term "solvent" is used herein to mean either water or an organic solvent or a mixture thereof. Water in this context includes not only mere water but also physiological saline, isotonized water, neutral, acidic, and basic buffer solutions, and aqueous ammonia, to name but a few. The organic solvent includes various alcohols such as methyl alcohol, ethyl alcohol, propyl alcohol, isopropyl alcohol, butyl alcohol, isobutyl alcohol, sec-butyl alcohol, tert-butyl alcohol, etc., halogenated hydrocarbons such as chloroform, methylene chloride, trichloroethane, etc., hydrocarbons such as hexane, benzene, toluene, etc., ethers, and ketones, among other solvents. Among these solvents, ethyl alcohol is preferred when effects on human physiology are taken into consideration. The mixture solvent includes various combinations of water with the organic solvents typically mentioned above. With any of such solvents, the composition of the invention can be manufactured.

It should be understood that when a solvent is used in the practice of the present invention, the use of water is sufficient for commercial-scale production of the composition of the invention. Thus, substantially speaking, the use of an organic solvent is unnecessary. This is one of the major characteristics of the present invention.

Though it depends on the other materials used, mode of production, extruder type and model, etc., the above-mentioned solvent can be added in a proportion of 1–80% (w/w) based on the total solid matter of the feed. The preferred proportion is 3–60% (w/w) and the still better proportion is 5–40% (w/w). When the proportion of the solvent is less than 1% (w/w), the advantage of use of the solvent may not be realized. On the other hand, when the proportion is greater than 60% (w/w), the consistency of the extrudate may be too soft for the ease of subsequent operations.

Where necessary, plasticizers and fluidizing agents which are conventionally used in pharmaceutical practice can be incorporated in suitable proportions. Such plasticizers and fluidizing agents help to reduce the unnecessarily high frictional resistance within the barrel to insure smooth extruder processing. These agents are useful in cases where a solvent is not used or cannot be used.

The maximum proportion of such plasticizers and/or fluidizing agents that can be tolerated is about 30% (w/w) based on the combined weight of said physiologically inert powdery additive and macromolecular additive. Although the composition of the present invention can be manufactured even if the above limit is exceeded, there are cases in which events unfavorable to the physical properties of the preparation, such as interadhesion of extrudates, poor disintegratability, etc., are encountered.

The plasticizer and fluidizing agent that can be used include various substances which are liquid at ordinary temperature, for example fatty acid derivatives such as triacetin, triethyl citrate, medium-chain fatty acid triglycerides, isopropyl myristate, fatty acid glycerol esters, etc.; alcohols such as propylene glycol, polyethylene glycol 200, polyethylene glycol 400, polyethylene glycol 600, glycerin, etc.; oleaginous substances such as liquid paraffin, hydrogenated oils, olive oil, orange oil, sesame oil, soybean oil, camellia oil, corn oil, rapeseed oil, coconut oil, peanut oil, etc.; and surfactants such as polyoxyethylene-hydrogenated castor oil, sorbitan sesquioleate, sorbitan trioleate, sorbitan monopalmitate, sorbitan monolaurate, polysorbates, and so on.

The extruder processing parameter settings are now described.

The temperatures of the barrel and die are dependent on the types of physiologically inert powdery additive, macromolecular additive, drug, solvent, plasticizer, fluidizing agent, and extruder type and model but can be set at 0°–150° C. and preferably at 30°–90° C. If the temperatures are below 0° C., the composition of the invention may not be obtained. If 150° C. is exceeded, the drug may decompose depending on its kind.

The screw speed (processing speed) can be properly selected according to the extruder type and model, feed, screw geometry, etc. and within the permissible range for the particular extruder used. The greater the overall length of the barrel, the higher can be the screw speed. This is because the longer the whole barrel is, the higher is the processing capacity of the extruder. To be specific, the screw speed can be set at 50 rpm or higher and is preferably set between 50 and 300 rpm.

The delivery pressure can be 10–150 kg/cm$^2$ and is preferably 30–120 kg/cm$^2$.

The screw geometry and combination are not too critical and can be rather liberally selected. However, it is desirable to select at least one element having a configuration conducive to high mixing and shear forces, i.e. the so-called kneading paddle (heading disk). The en bloc processing with such a kneading paddle contributes to improved physiochemical stability of the drug and preparation thanks to the high heading and shear forces it delivers.

The extrusion die can be changed according to the intended preparation comprising the composition of the invention (hereinafter referred to as the preparation of the invention). Thus, a circular extrusion die having a suitable orifice diameter for the production of a cylindrical extrudate and a flat extrusion die for production of a tabular extrudate can be mentioned as examples. In any event, regardless of die configuration, drugs can be physicochemically stabilized and the composition and preparation of the invention can be successfully provided.

The preparation of the invention may be any form that is capable of carrying the composition of the invention and is not limited to any particular form. Thus, granules, fine granules, powders, capsules, and tablets containing the composition of the invention can be mentioned by way of example.

The preparation of the invention can be manufactured in the following manner.

The feed processed en bloc by the extruder emerges from the die as a continuous artefact. This artefact can be cut to length with a roller mill, a cutter mill, a pin mill, or the like. The cuttings can be directly used as the granular or fine granular preparation of the invention. The composition of the invention as extruded from the die can be cut to length with a rotary cutter mounted at the front end of the die (e.g. a two-blade rotary cutter operable over the range of 0–1750 rpm), whereby the granular or fine granular preparation of the invention can be provided without resort to any special sieving for size selection.

The capsular preparation of the invention can be provided by filling capsule shells with the above granular or fine granular composition of the invention. Moreover, by compressing the composition, the tabular preparation (tablets) of the invention can be provided.

Furthermore, the composition of the invention as extruded from the die, the granular or fine granular cuttings thereof, or the compressed composition of the invention can be coated and supplied either as it is or filled in capsule shells to provide the capsular preparation of the invention. In this connection, by using various performance coatings each yielding a water-soluble film, an insoluble film, a gastric coating film, or an enteric coating film, there can be provided preparations of the invention which have a variety of functions.

BEST MODE FOR CARRYING OUT THE INVENTION

The following examples, comparative examples, and test examples are intended to illustrate the present invention in further detail. It should be understood that the scope of the invention is not limited to the specific examples herein presented.

EXAMPLE 1

Using a compact kneader (KDH-3, Fuji Denki Kogyo, K.K.; the same applies hereinafter), 4 g of GASN, 500 g of lactose, 400 g of corn starch, and 100 g of crystalline cellulose, all passed through a 100-mesh sieve, were mixed and kneaded with 100 ml of 20% aqueous solution of polyvinyl alcohol for 10 minutes. This kneaded mass was fed to a twin-screw extruder (KEXN-30S-20, Kurimoto Iron Works Ltd.; the same applies hereinafter) equipped with screws each having a diameter of 32 mm$\phi$, an effective L/D ratio of 20, and a screw pattern of 16 P, 12 P, 9.6 P, 30 deg, 60 deg, 9.6 P, and 8 P and a 0.7 mm$\phi$×8-orifice die via its main feeding port at a rate of 30 g/min. and processed at a barrel temperature of 50° C., a die temperature of 50° C., and a screw speed of 80 rpm. The extrudate was dried at 45° C. to provide a GASN composition.

EXAMPLE 2

Using a TK homomixer (HUM; Tokushu Kika Kogyo, K.K.; the same applies hereinafter), a GASN suspension was prepared from 4 g of GASN, 20 g of hydroxypropylmethylcellulose, both passed through a 100-mesh sieve, and 100 g of purified water. This suspension was fed to a compact kneader containing 1000 g of lactose and compounded for 10 minutes. The resulting compound was fed to a twin-screw extruder equipped with screws each having a diameter of 32 mm$\phi$, an effective L/D ratio of 20, and a screw pattern of 16 P, 12 P, 9.6 P, 30 deg, 60 deg, 9.6 P, and 8 P and a 1.0 mm$\phi$×5-orifice die via its main feeding port at a rate of 30 g/min. and processed at a barrel temperature of 50° C., a die temperature of 50° C., and a screw speed of 100 rpm. The extrudate was dried at 45° C. to provide a GASN composition.

EXAMPLE 3

A mixture of 8 g of GASN, 1200 g of lactose, 700 g of corn starch, and 100 g of low-substituted hydroxypropylcellulose, all passed through a 100-mesh sieve, was fed to a twin-screw extruder equipped with screws each having a diameter of 32 mm$\phi$, an effective L/D ratio of 20, and a screw pattern of 16 P, 12 P, 9.6 P, 30 deg, 60 deg, 9.6 P, and 8 P and a 0.5 mm$\phi$×15-orifice die via its main feeding port at a rate of 40 g/min., while 30% aqueous solution of polyvinylpyrrolidone was fed via the auxiliary feeding port disposed between the barrel zone 1 (main feed barrel) and barrel zone 2 of the extruder at a rate of 4 g/min., and the whole feed was processed at a barrel temperature of 50° C., a die temperature of 50° C., and a screw speed of 100 rpm. The extrudate was dried at 45° C. to provide a GASN composition.

EXAMPLE 4

Using a TK homomixer, a GASN solution was prepared from 4 g of GASN, 20 g of hydroxypropylcellulose, 50 g of purified water, and 50 g of ethanol. This solution was fed to a compact kneader containing 1000 g of D-mannitol and kneaded for 10 minutes. The kneaded mass was fed to a twin-screw extruder equipped with screws each having a diameter of 32 mm$\phi$, an effective L/D ratio of 20, and a screw pattern of 16 P, 12 P, 9.6 P, 30 deg, 60 deg, 9.6 P, and 8 P and a 1.0 mm$\phi$×5-orifice die via its main feeding port at a rate of 30 g/min. and processed at a barrel temperature of 50° C., a die temperature of 50° C., and a screw speed of 100 rpm. The extrudate was died at 45° C. to provide a GASN composition.

EXAMPLE 5

The GASN composition obtained in Example 1 was sieved for size selection using a feather mill (FM-1, Hosokawa Microns Co., Ltd.; the same applies hereinafter) equipped with a 12-mesh screen at 900 rpm to provide GASN granules according to the present invention.

EXAMPLE 6

The GASN composition obtained in Example 2 was processed in a feather mill equipped with a 16-mesh screen at 3500 rpm. Using a capsule filling machine (No. 8 Capsule Filler, Nippon Elanco, K.K.; the same applies hereinafter), about 500 mg each of the resulting granules were filled into No. 0 capsules to provide GASN capsules according to the present invention.

EXAMPLE 7

The GASN composition obtained in Example 3 was processed in a feather mill equipped with a 16-mesh screen at 3500 rpm. To 1000 g of the resulting granules was added 5 g of magnesium stearate and the mixture was blended in a twin-shell blender (FM-V-10, Fuji Sangyo, K.K.; the same applies hereinafter) for 20 minutes. The resulting granules were compressed with a double-pressure-stage tablet machine (Cleanpress Correct 12HUK; Kikusui Seisakusho, Ltd.; the same applies hereinafter) set at a diameter of 9.0 mm$\phi$ and a tablet weight of abut 250 mg to provide GASN tablets according to the present invention.

EXAMPLE 8

The GASN composition obtained in Example 4 was sieved for size selection using a feather mill equipped with a 10-mesh screen at 900 rpm to provide GASN granules for gargle use according to the present invention.

EXAMPLE 9

Using a twin-shell blender, 4 g of finely divided L-menthol, 150 g of corn starch, 156 g of D-mannitol, 10 g of hydroxypropylcellulose, and 80 g of polyethylene glycol 6000, all passed through a 200-mesh sieve, were mixed for 20 minutes. This powdery mixture was fed to a twin-screw extruder equipped with screws each having a diameter of 32 mm$\phi$, an effective L/D ratio of 20, and a screw pattern of 16 P, 12 P, 9.6 P, 30 deg, 60 deg, 9.6 P, and 8 P and a 0.7 mm$\phi$ 8-orifice die via its main feeding port at a rate of 30 g/min. and processed at a barrel temperature of 55° C., a die temperature of 30° C., and a screw speed of 80 rpm to provide an L-menthol composition. The composition was further subjected to size selection using a feather mill equipped with a 10-mesh screen at 900 rpm to provide L-menthol granules according to the present invention.

EXAMPLE 10

Using a twin-shell blender, 800 g of ethenzamide, 5 g of chlorpheniramine maleate, 20 g of noscapine, 20 g of dl-methylephedrine hydrochloride, 100 g of guaiacol sulfonate potassium, 60 g of caffeine, 355 g of lactose, 368 g of corn starch, 72 g of hydroxypropylcellulose, 480 g of polyethylene glycol 6000, and 120 g of stearic acid powder were mixed for 20 minutes. A 200 g portion of this powdery mixture was fed to a twin-screw extruder equipped with screws each having a diameter of 32 mm$\phi$, an effective L/D ratio of 20, and a screw pattern of 16 P, 12 P, 9.6 P, 30 deg, 60 deg, 9.6 P, and 8 P and a 1.0 mm$\phi$×5-orifice die via its main feeding port at a rate of 30 g/min. and processed at a barrel temperature of 60° C., a die temperature of 30° C., and a screw speed of 80 rpm to provide a medicinal composition. This medicinal composition was further subjected to size selection in a feather mill equipped with a 12-mesh screen at 900 rpm to provide common cold remedy granules according to the present invention.

EXAMPLE 11

Using a twin-shell blender, 60 g of pipethanate hydrochloride, 234 g of lactose, 156 g of corn starch, and 150 g of stearic acid powder, all passed through a 100-mesh sieve, were mixed for 20 minutes. A 200 g portion of this powdery mixture was fed to a twin-screw extruder equipped with screws each having a diameter of 32 mm$\phi$, an effective L/D ratio of 20, and a screw pattern of 16 P, 12 P, 9.6 P, 30 deg, 60 deg, 9.6 P, and 8 P and a 0.7 mm$\phi$×8-orifice die via its main feeding port at a rate of 30 g/min. and processed at a barrel temperature of 70° C., a die temperature of 40° C., and a screw speed of 80 rpm to provide a medicinal composition. This medicinal composition was sieved for size selection in a feather mill equipped with a 10-mesh screen at 900 rpm to provide pipethanate hydrochloride granules according to the present invention.

EXAMPLE 12

Using a twin-shell blender, 160 g of sodium valproate, 160 g of dry aluminum hydroxide gel, 150 g of polyethylene glycol 6000, 60 g of stearic acid powder, 100 g of hydrous silicon dioxide, and 10 g of hydroxypropylcellulose were mixed for 20 minutes. This powdery mixture was fed to a twin-screw extruder equipped with screws each having a diameter of 32 mm$\phi$, an effective L/D ratio of 20, and a screw pattern of 16 P, 12 P, 9.6 P, 30 deg, 60 deg, 9.6 P, and 8 P and a 1.0 mm$\phi$×5-orifice die via its main feeding port at a rate of 30 g/min. and processed at a barrel temperature of 60° C., a die temperature of 30° C., and a screw speed of 80 rpm to provide a medicinal composition. This medicinal composition was further sieved for size selection in a feather mill equipped with a 12-mesh screen at 900 rpm to provide sodium valproate granules according to the present invention.

COMPARATIVE EXAMPLE 1

A portion of the kneaded mass obtained with a compact kneader in Example 1 was extruded from an ordinary single-screw granulator (ECK Pelleter EXK-1, Fuji Denki K.K.; the same applies hereinafter) equipped with a 0.7 mm$\phi$ screen at a rate of 30 rpm and dried at 45° C. The dried extrudate was then sieved for size selection in a feather mill equipped with a 12-mesh screen at 900 rpm to provide reference GASN granules.

COMPARATIVE EXAMPLE 2

A portion of the kneaded mass obtained with a compact kneader in Example 2 was extruded from an ordinary single-screw granulator equipped with a 1 mm$\phi$ screen at a rate of 30 rpm and dried at 45° C. The dried extrudate was then milled in a feather mill equipped with a 16-mesh screen at 3500 rpm and using a capsule filling machine, about 500 mg aliquots of the resulting particulate composition were filled into No. 0 capsule shells to provide reference GASN capsules.

COMPARATIVE EXAMPLE 3

Using a compact kneader, 4.8 g of GASN, 720 g of lactose, 420 g of corn starch, and 60 g of low-substituted hydroxypropylcellulose, all passed through a 100-mesh sieve, were mixed and kneaded with 150 ml of 30% aqueous solution of polyvinylpyrrolidone for 10 minutes and then dried at 45° C. The dry kneaded mass was pulverized in a feather mill equipped with a 16-mesh screen at 3500 rpm. To 1000 g of the resulting granules was added 5 g of magnesium stearate and the mixture was treated in a twin-shell blender for 20 minutes. The resulting tablet-making granules were compressed using a double-pressure-stage tablet machine into tablets having a diameter of 9.0 mm$\phi$ and each weighing abut 250 mg to provide reference GASN tablets.

COMPARATIVE EXAMPLE 4

A portion of the kneaded mass obtained with a compact kneader in Example 4 was extruded from an ordinary single-screw granulator equipped with a 1 mm$\phi$ screen at a rate of 30 rpm and dried at 45° C. The dried extrudate was then pulverized in a feather mill equipped with a 10-mesh screen at 900 rpm to provide reference GASN granules for gargle use.

COMPARATIVE EXAMPLE 5

Using a compact kneader, 225 g of corn starch, 234 g of D-mannitol, and 120 g of polyethylene glycol 6000 were mixed and kneaded with 50 ml of a solution of 6 g L-menthol and 15 g hydroxypropylcellulose in ethanol for 10 minutes. The resulting kneaded mass was extruded from an ordinary single-screw granulator equipped with a 0.7 mm$\phi$ screen at a rate of 30 rpm and dried in a fluidized-bed granulator (STREA-1, Fuji Sangyo K.K.; the same applies hereinafter) at 40° C. The dry granules were then sieved for size selection in a feather mill equipped with a 10-mesh screen to provide reference L-menthol granules.

COMPARATIVE EXAMPLE 6

The powdery mixture obtained by using a twin-shell blender in Example 9 was used as a reference sample.

COMPARATIVE EXAMPLE 7

Using a compact kneader, a portion of the powdery mixture obtained in Example 10 was kneaded with 10% aqueous solution of hydroxypropylcellulose for 10 minutes. The headed mass was extruded from an ordinary single-screw granulator equipped with a 1.0 mm$\phi$ screen at a rate of 30 rpm and dried in a fluidized-bed granulator at 50° C. The dry granules were further sieved for size selection in a feather mill equipped with a 12-mesh screen at 900 rpm to provide reference cold remedy granules.

COMPARATIVE EXAMPLE 8

Using a compact kneader, a portion of the powdery mixture obtained in Example 11 was kneaded with 10% aqueous solution hydroxypropylmethylcellulose for 10 minutes. The kneaded mass was extruded from an ordinary single-screw granulator equipped with a 0.7 mm$\phi$ screen at a rate of 30 rpm and dried in a fluidized-bed granulator at 50° C. The dry granules were sieved for size selection in a feather mill equipped with a 10-mesh screen at 900 rpm to provide reference pipethanate HCl granules.

COMPARATIVE EXAMPLE 9

The powdery mixture obtained in Example 11 was used as a reference powdery mixture sample.

COMPARATIVE EXAMPLE 10

Using a compact kneader, a portion of the powdery mixture obtained in Example 12 was kneaded with 10% aqueous solution of hydroxypropylcellulose for 10 minutes. The kneaded mass was extruded from an ordinary single-screw granulator equipped with a 1.0 mm$\phi$ screen at a rate of 30 rpm and dried in a fluidized-bed granulator at 50° C. The dried granules were further sieved for size selection in a feather mill equipped with a 12-mesh screen at 900 rpm to provide reference sodium valproate granules.

TEST EXAMPLE 1 GASN

The GASN granules, capsules, tablets, and gargle granules obtained in Examples 5–8 in accordance with the present invention, the reference GASN granules, capsules, tablets, and gargle granules obtained in Comparative Examples 1–4, and GASN bulk substance were respectively put in polyethylene bottles and stored under accelerated aging temperatures of 40° C. and 50° C. for 4 weeks. Serial sampling was made and the stability of GASN in each preparation was evaluated.

Assays were carried out by measuring the absorbance at 568 nm in phosphate buffer solution at pH 7.0 and the residual amount of GASN was calculated by means of the following equation.

$$\text{Amount of } GASN \text{ (mg)} = \frac{A}{20.25} \times 1000$$

The results are shown in Tables 1 and 2.

TABLE 1

Percent residues of GASN exposed to accelerated aging conditions (40° C.)

| Example | Immediately after preparation | Week 1 | Week 2 | Week 3 | Week 4 |
|---|---|---|---|---|---|
| Example 5 | 100 | 99.8 | 98.6 | 98.0 | 97.2 |
| Example 6 | 100 | 99.6 | 99.7 | 99.4 | 99.1 |
| Example 7 | 100 | 99.7 | 98.5 | 98.6 | 98.3 |
| Example 8 | 100 | 99.6 | 99.8 | 99.4 | 99.3 |
| Comparative Example 1 | 100 | 87.4 | 66.2 | 51.4 | 40.8 |
| Comparative Example 2 | 100 | 91.7 | 78.2 | 63.8 | 45.2 |
| Comparative Example 3 | 100 | 90.2 | 56.7 | 47.6 | 39.7 |
| Comparative Example 4 | 100 | 98.6 | 90.4 | 74.8 | 69.3 |
| Bulk substance | 100 | 63.5 | 31.4 | 6.3 | 0 |

TABLE 2

Percent residues of GASN exposed to accelerated aging conditions (50° C.)

| Example | Immediately after preparation | Week 1 | Week 2 | Week 3 | Week 4 |
|---|---|---|---|---|---|
| Example 5 | 100 | 99.6 | 98.7 | 96.2 | 95.6 |
| Example 6 | 100 | 99.8 | 99.6 | 98.2 | 96.4 |
| Example 7 | 100 | 99.7 | 98.5 | 96.7 | 94.8 |
| Example 8 | 100 | 99.7 | 99.4 | 98.9 | 98.2 |
| Comparative Example 1 | 100 | 61.7 | 43.7 | 5.1 | 0 |
| Comparative Example 2 | 100 | 73.3 | 60.2 | 11.3 | 0 |
| Comparative Example 3 | 100 | 56.6 | 39.7 | 2.3 | 0 |
| Comparative Example 4 | 100 | 87.6 | 81.2 | 68.3 | 49.5 |
| Bulk substance | 100 | 41.2 | 3.4 | 0 | 0 |

It is apparent from Tables 1 and 2 that the preparation manufactured by using a twin-screw extruder according to the present invention, without regard to the mode of addition of GASN (Examples 5 and 7: addition in powder form; Example 6: addition in suspension form; Example 8: addition in solution form), remained stable on prolonged exposure to the accelerated aging condition of 40° C. or 50° C. as compared with GASN bulk substance, the granules prepared using an ordinary single-screw granulator (Comparative Examples 1, 2 and 4) or the tablet prepared mainly by the conventional kneading method (Comparative Example 3).

TEST EXAMPLE 2 L-MENTHOL

The preparation of Example 9, the reference preparation of Comparative Example 5, and the reference powdery mixture or kneaded powder of Comparative Example 6 were respectively placed, about 20 mm deep, in glass dishes and stored under the accelerated aging temperature condition of 40° C. for 4 weeks. Samples were serially taken for the assay of L-menthol. Assays were carried out in conformity with the Japanese Pharmacopoeia. The results are shown in Table 3.

TABLE 3

Percent residues of L-menthol exposed to accelerated aging conditions (40° C.)

| Example | Immediately after preparation | Week 1 | Week 2 | Week 3 | Week 4 |
|---|---|---|---|---|---|
| Example 9 | 100 | 96.8 | 92.3 | 87.7 | 79.4 |
| Comparative Example 5 | 100 | 47.6 | 27.6 | 14.4 | 7.1 |
| Comparative Example 6 | 100 | 37.7 | 19.9 | 8.6 | 0.7 |

For each sample, the value immediately after preparation was taken as 100%.

It is apparent from Table 3 that the preparation manufactured by using a twin-screw extruder according to the present invention showed a smaller amount of dissipation compared with the reference preparation and reference powdery mixture. Therefore, it is clear that the method of the present invention is useful for drugs which are sublimable and liable to undergo considerable losses of content.

TEST EXAMPLE 3 ETHENZAMIDE AND CAFFEINE

The granules obtained in Example 10 and Comparative Example 7 were respectively filled in 20 ml vials, 10 g per vial, and each filled vial was stoppered with a rubber stopper and sealed with an aluminum cap (3 vials each were provided). The sealed vials were stored at the accelerated aging temperature of 50° C. for 3 months and the development of whiskers was examined under the light microscope. The results are shown in Table 4.

TABLE 4

Incidence of whiskers under accelerated aging conditions (50° C.)

| Example | Immediately after preparation | Month 1 | Month 2 | Month 3 |
|---|---|---|---|---|
| Example 10 | – | – | ± | ± |
| Comparative Example 7 | – | +1 | +2 | +3 |

Criteria
–: No whiskers
±: Doubtful
+1: 1–3 whiskers per granule
+2: More than 3 whiskers per granule
+3: Abundant whiskers in vial It is apparent from Table 4 that the preparation manufactured by using a twin-screw extruder according to the present invention showed only a slight amount of whiskers even after 3 months of storage. In contrast, the reference preparation had developed a substantial amount of whiskers within one-month period and showed abundant whiskers full of the vial after 3 months.

Therefore, it is clear that the present invention provides a technology by which the development of whiskers can be inhibited very expediently through use of a twin-screw extruder.

TEST EXAMPLE 4 PIPETHANATE HYDROCHLORIDE

To 10 g each of the preparation of the invention as obtained in Example 11, the reference preparation obtained in Reference Example 8, and the reference powdery mixture obtained in Example 9 was added 2 g of magnesium oxide JP and the mixture was thoroughly blended in a polyethylene bag and placed, abut 10 mm deep, in a 70 mm (in. dia.) glass dish. Each sample was stored under the accelerated aging conditions of 40° C. and 75% RH for 4 weeks and serially sampled to determine the pipethanate HCl content. Assays were carried out by HPLC and absorptiometry at 259 nm. The results are shown in Table 5.

TABLE 5

Percent residues of pipethanate hydrochloride exposed to accelerated aging conditions (40° C, 75% RH)

| Example | Immediately after preparation | Week 1 | Week 2 | Week 3 | Week 4 |
|---|---|---|---|---|---|
| Example 11 | 100 | 98.8 | 94.2 | 85.3 | 82.2 |
| Comparative Example 8 | 100 | 55.2 | 38.4 | 32.6 | 21.1 |
| Comparative Example 9 | 100 | 45.2 | 26.8 | 20.2 | 17.4 |

For each sample, the value immediately after preparation was taken as 100%.

It is apparent from Table 5 that in the stability of pipethanate hydrochloride, the preparation manufactured by using a twin-screw extruder according to the present invention was superior to the reference preparation manufactured by using the single-screw granulator which is conventionally used for the manufacture of granules even under the accelerated aging conditions of 40° C. and 75% R.H.

TEST EXAMPLE 5 SODIUM VALPROATE

The preparation of the invention as obtained in Example 12 and the reference preparation obtained in Comparative Example 10 were respectively placed, abut 10 mm deep, in 70 mm (in. dia.) glass dishes and stored under the accelerated aging conditions of 40° C. and 75% R.H. for 4 weeks, and the degree of moisture absorption was serially examined. Separately, 2 g each of the preparation of the invention, reference preparation, and powdery mixture obtained in Example 12 were placed in glass weighing bottles and allowed to sit at 40° C., 75% R.H. and the amount of water absorption was serially determined. The results are shown in Table 6 and FIG. 1.

TABLE 6

| | Hygroscopicity under accelerated aging conditions (40° C., 75% RH) | | | | |
|---|---|---|---|---|---|
| | Immediately after | Week | | | |
| Example | preparation | Week 1 | Week 2 | Week 3 | Week 4 |
| Example 12 | − | − | − | ± | − |
| Comparative Example 10 | − | ± | +1 | +2 | +2 |

Criteria
−: Free-flowing
±: Doubtful
+1: Intergranular adhesion found but flowable
+2: Intergranular adhesion forming blocks, not flowable.

Figure 1:
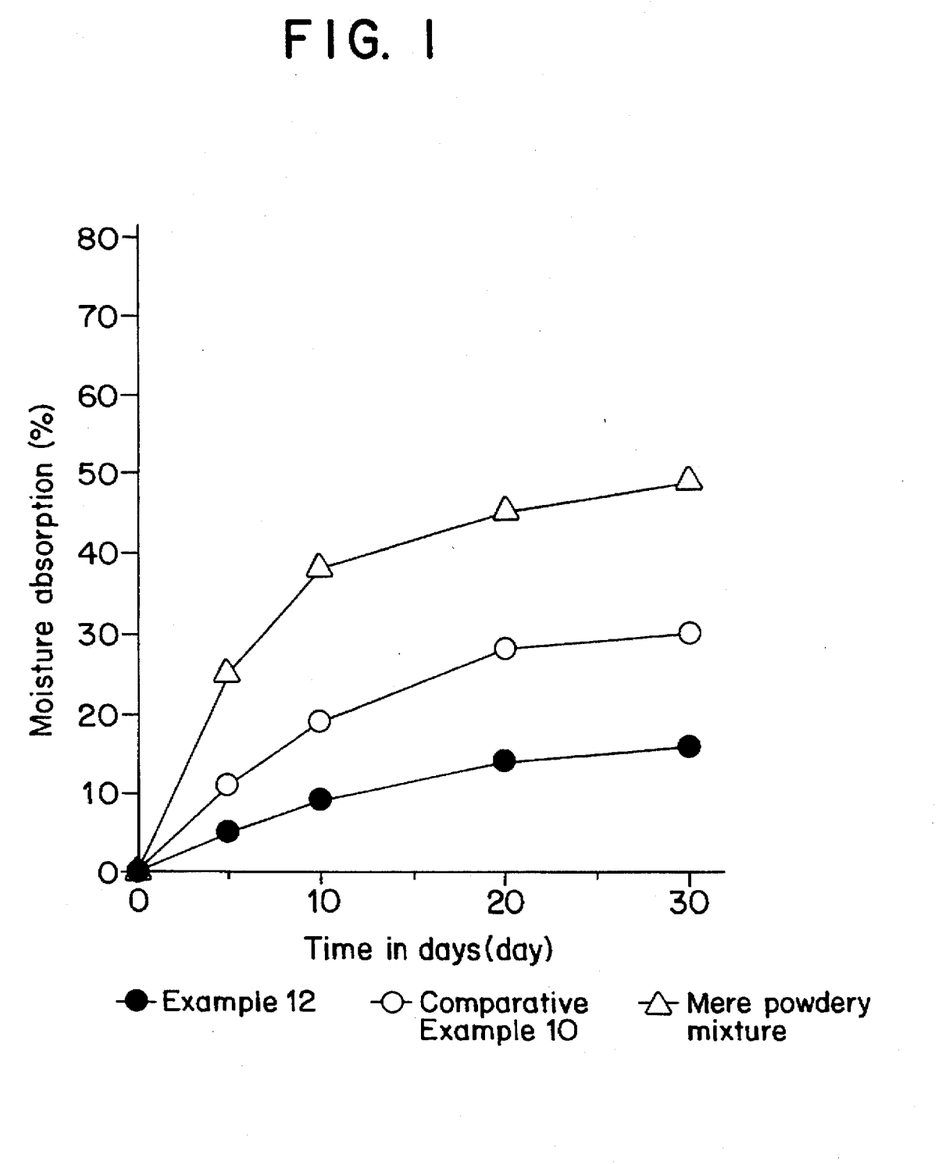
FIG. 1 shows the hygroscopicity of sodium valproate preparations. The ordinate represents moisture absorption (%) and the abscissa represents time in days.

It is apparent from Table 6 and FIG. 1 that the preparation manufactured by using a twin-screw extruder according to the present invention showed an apparent inhibition of moisture absorption compared with the preparation (reference preparation) manufactured by using the single-screw granulator which is conventionally used for the manufacture of granules even when stored under the accelerated aging conditions of 40° C. and 75% R.H.

EFFECT OF THE INVENTION

In accordance with the present invention, a physicochemically stable pharmaceutical composition can be manufactured expediently, rapidly, on a mass scale, and basically continuously. Thus, drugs and preparations can be physicochemically stabilized by the technology of the invention which is both practically and economically advantageous. Furthermore, since the composition of the invention can be manufactured substantially without use of any organic solvent, the invention provides a highly safe production method.

BRIEF DESCRIPTION OF THE DRAWING

The closed circle ● represents data for the sodium valproate granule according to Example 12, the open circle ○ represents data for the sodium valproate granule according to Comparative Example 10, and the open triangle △ represents data for the mere powdery mixture according to Example 12.

We claim:
1. A method of increasing the physicochemical stability of a drug substance, comprising:
providing ingredients comprising 1 part by weight of a physiologically inert powdery additive, 0.001–1 part by weight of a macromolecular additive per part by weight of said physiologically inert additive, and a drug substance selected from the group consisting of subliminal drug, volatile drug, drug hydrolyzable in the presence of water, drug with tendency to develop whiskers, hygroscopic drug, and deliquescent drug; and processing said ingredients en bloc by means of a multi-screw extruder to produce a pharmaceutical composition containing said drug substance, wherein the substance in the composition exhibits increase physicochemical stability.

2. The method of claim 1, wherein the multi-screw extruder is a twin-screw extruder.

3. The method of claim 1, wherein said macromolecular additive is 0.005 to 0.9 part by weight per part by weight of said physiologically inert powdery additive.

4. The method of claim 1, wherein said drug substance is 0.0001–10 times, by weight, the combined amount of said inert powdery additive and macromolecular additive.

5. The method of claim 4, wherein said drug substance is 0.001–5 times, by weight, the combined amount of said physiologically inert powdery additive and macromolecular additive.

6. The method of claim 5, wherein said drug substance is 0.01–1 times, by weight, the combined amount of said physiologically inert powdery additive and macromolecular additive.

7. The method of claim 1, wherein said drug substance is selected from the group consisting of drug hydrolyzable in presence of water, hygroscopic drug, and deliquescent drug, the method further comprising the step of adding a solvent to said ingredients prior to or during said en bloc processing.

8. The method of claim 1, wherein said drug substance is selected from the group consisting of subliminal drug, volatile drug, and drug with tendency to develop whiskers, the method further comprising the step of adding a plasticizer or a fluidizing agent to said ingredients prior to or during said en block processing.

9. The method of claim 1, wherein said drug substance is the sublimable drug selected from the group consisting of sodium 1,4-dimethylisopropyl-azulene-3-sulfonate, L-menthol, paraform, trimethadione, camphor, and naphthalene.

10. The method of claim 1, wherein said drug substance is the volatile drug selected from the group consisting of cinnamyl alcohol, anethole, eugenole, cinnamon oil, eucalyptus oil, lemon oil, fennel oil, clove oil, and mint oil.

11. The method of claim 1, wherein said drug substance is the drug hydrolyzable in the presence of water selected from the group consisting of aspirin, pipethanate hydrochloride, L-ethylcysteine hydrochloride, pyridostigmine bromide, calcium pantothenate, mepitiostane, pentobarbital sodium, and trichloroisocyanuric acid.

12. The method of claim 1, wherein said drug substance is the drug which develops whiskers and is selected from the group consisting of ethenzamide, caffeine, acetaminophen, bromvalerylurea, and clofedanol hydrochloride.

13. The method of claim 1, wherein said drug is the hygroscopic or deliquescent drug and is selected from the group consisting of sodium valproate, cyanocobalamin, diethylcarbamazine citrate, isosorbide, diclofenac sodium, betahistine mesylate, carpronium chloride, tolazoline hydrochloride, reserpilic acid dimethylaminoethyl ester dihydrochloride, carbachol, choline theophyllinate, choline salicylate, citicoline, hexamethonium bromide, chlorophyllin sodium-copper salt, panthenol, dexamethazone phosphate disodium salt, plant extracts, procainamide hydrochloride, L-proline, and calcium chloride.

14. A pharmaceutical composition produced by the method of claim 1.

* * * * *